United States Patent [19]

Gustilo

[11] Patent Number: 4,463,753

[45] Date of Patent: Aug. 7, 1984

[54] COMPRESSION BONE SCREW

[76] Inventor: Ramon B. Gustilo, 701 Park Ave., Minneapolis, Minn. 55415

[21] Appl. No.: 301,415

[22] Filed: Sep. 11, 1981

Related U.S. Application Data

[63] Continuation-in-part of Ser. No. 109,639, Jan. 4, 1980, abandoned.

[51] Int. Cl.³ ............................................... A61F 5/04
[52] U.S. Cl. .............................. 128/92 B; 128/92 BC; 128/92 BB
[58] Field of Search ............ 128/92 B, 92 BC, 92 BB, 128/92 R

[56] References Cited

U.S. PATENT DOCUMENTS

| | | | |
|---|---|---|---|
| 2,382,019 | 8/1945 | Miller | 128/92 B |
| 2,489,870 | 11/1949 | Dzus | 128/92 B |
| 2,494,229 | 1/1950 | Collison | 128/92 B |
| 3,915,162 | 10/1975 | Miller | 128/92 R |
| 4,059,102 | 11/1977 | Devas | 128/92 B |
| 4,175,555 | 11/1979 | Herbert | 128/92 B |

Primary Examiner—C. Fred Rosenbaum
Assistant Examiner—C. W. Shedd
Attorney, Agent, or Firm—Sherman & Shalloway

[57] ABSTRACT

A compression screw having a proximal portion and a distal portion integrally interconnected by an intermediate tapering portion. The proximal and distal portions have threads of the same pitch. The intermediate portion has a smooth outer surface tapering the larger diameter proximal portion into the smaller diameter distal portion. The shaft of the proximal portion is cylindrical and the shaft of the distal portion is tapered, terminating in a sharp trocar point, and the threads of the proximal and distal portion may be provided with self-cutting flutes. The smooth tapering surface of the intermediate portion cooperates with the threads at the distal end to effect counteracting forces which cause compressions of the bone between the distal end and the taper.

13 Claims, 9 Drawing Figures

U.S. Patent  Aug. 7, 1984  Sheet 1 of 2  4,463,753
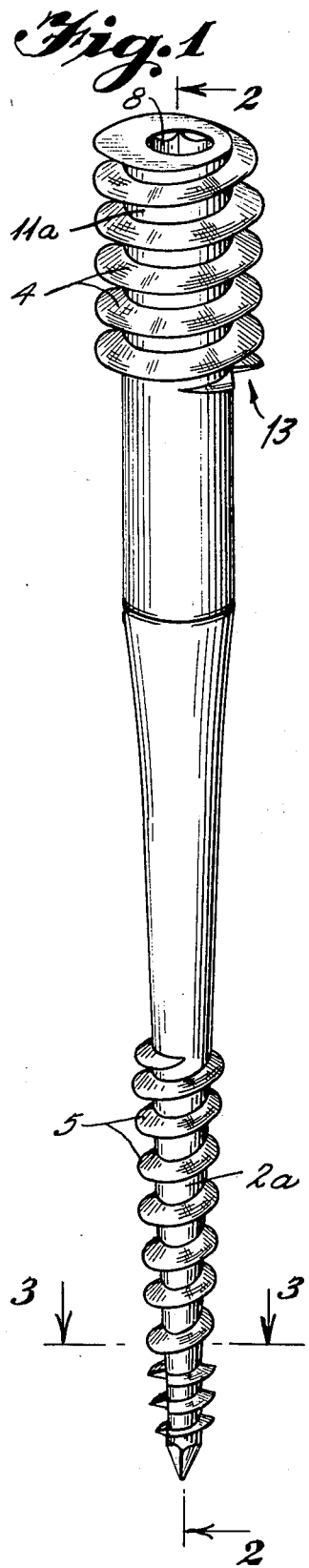
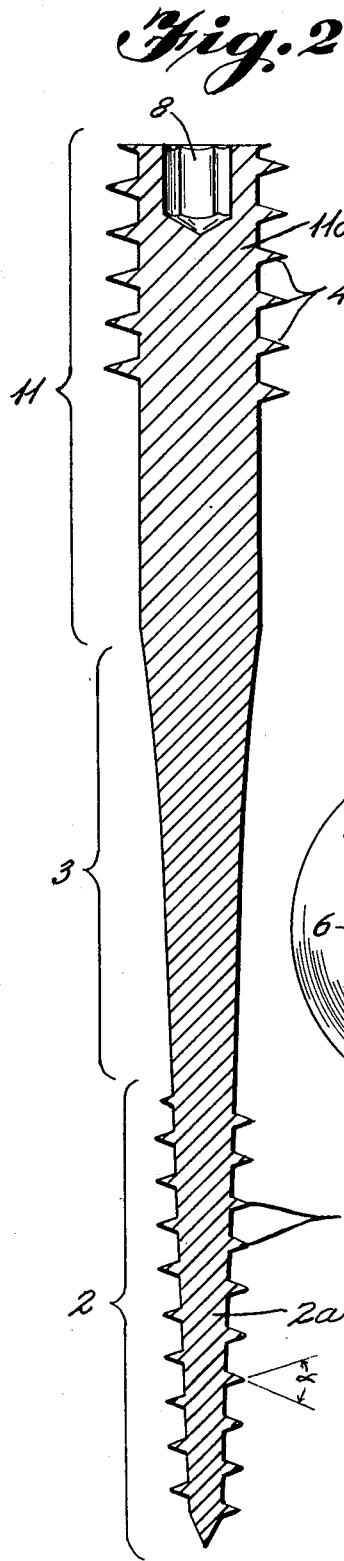
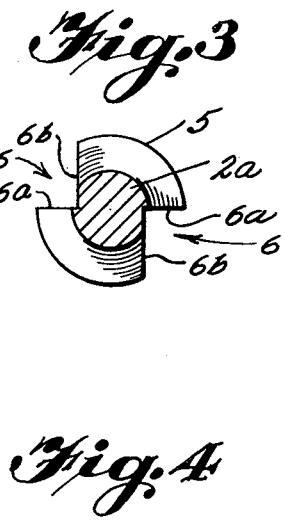
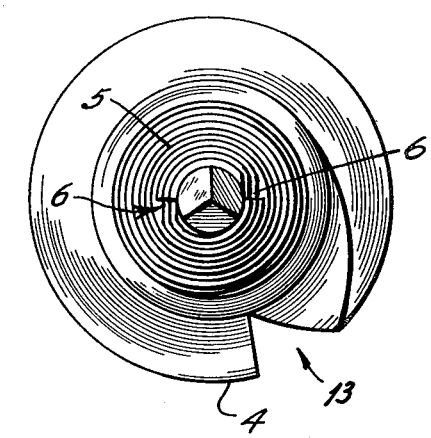

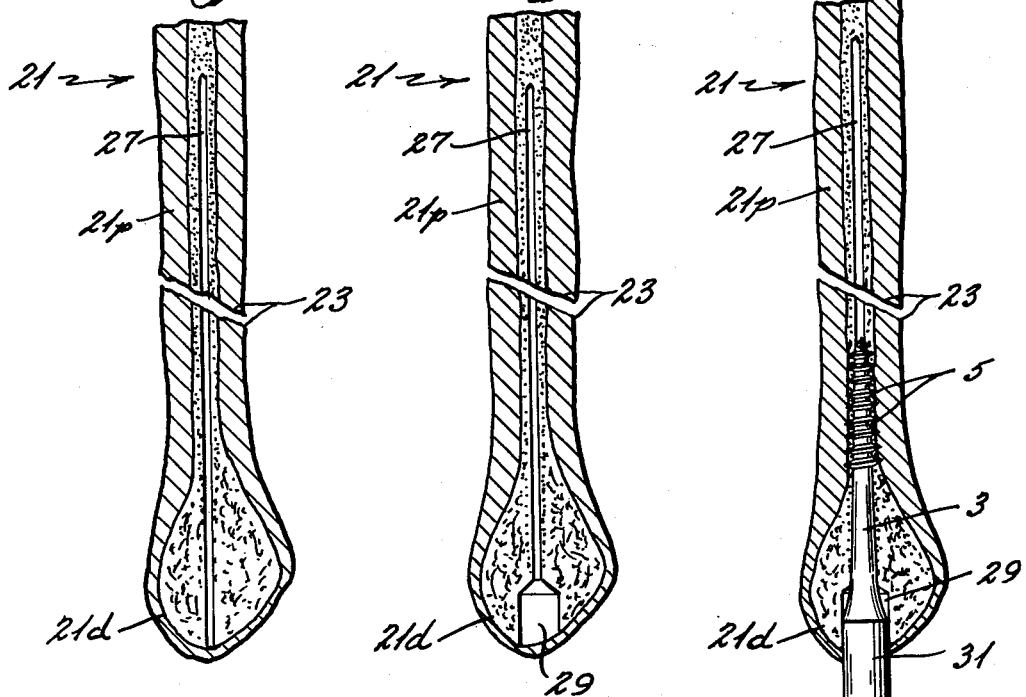
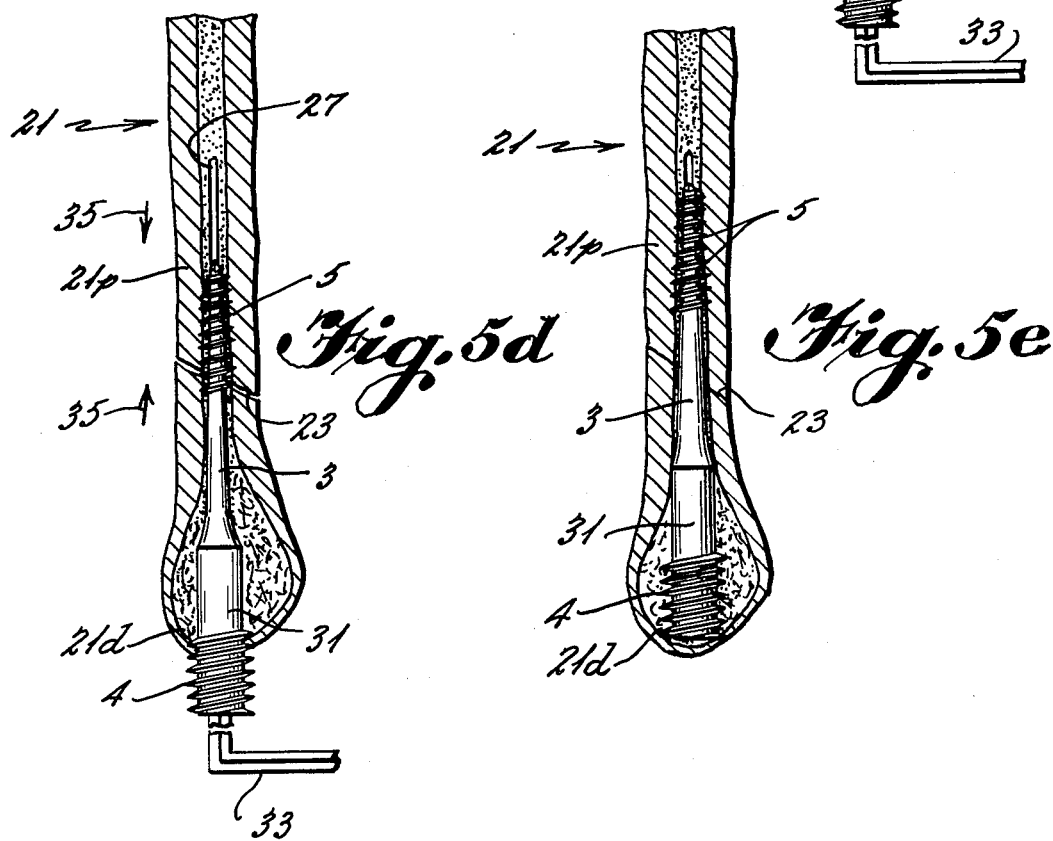

COMPRESSION BONE SCREW

This application is a continuation-in-part of Ser. No. 109,639, filed Jan. 4, 1980, now abandoned.

BACKGROUND OF THE INVENTION

1. Field of the Invention

The invention generally relates to a screw for joining parts of bone.

Many types of bone fractures, particularly fractures of the fibula are lateral fractures occurring near the distal end of a long bone. In such a case, if reinforcement is necessary, it may be desired to provide such reinforcement parallel to the length of the bone. In particular, this invention is directed to the provision of reinforcement, with a compressive force, along the medullary canal of the long bone, with access to the medullary canal being achieved by drilling along the center of the bone from the end of the bone.

While most fractures of long bones are transverse fractures, such fractures usually do not occur along lines perpendicular to the length of the bone, but rather occur along fracture lines which cross the bone in a diagonal direction. Thus, direct compressive force in many cases tends to cause the segments of the bone to shift laterally, thus defeating the purpose of intentionally applied compressive force. For this reason, any device effecting longidutinal compression at a fracture site must also provide a means for aligning the two segments of the bone so as to avoid any lateral shift.

2. Description of the Prior Art

Many types of screws are known in the prior art. For example, Russell in U.S. Pat. No. 146,023 describes a wood screw with a thread of varying pitch gradually decreasing from the point of the screw.

Fracture screw adjusting means are also known in the prior art as described by Charnley in U.S. Pat. No. 2,801,631.

Anchoring arrangements for joining two dissimilar materials are disclosed in Canadian Pat. No. 731,381, issued to Fischer.

None of the above-disclosed attaching structures have been particularly applied to use as a distal fibular screw.

A screw described by Herbert in U.S. Pat. No. 4,175,555 has two threads, separately located at different locations along the length of the screw at distal and proximal ends, respectively, the threads being separated by a shank portion. The distal threaded portion has a diameter which is smaller than the proximal threaded portion, while the thread pitch of the (narrow) distal threaded portion is greater than the thread pitch of the (wide) proximal threaded portion. This thread pitch differential causes the distal end of the screw to attempt to advance through bone tissue for each clockwise turn of the screw at a rate greater than the rate of advance of the proximal end of the screw. The difference in advance rates results in the compression of bone at the distal end against bone at the proximal end. It can therefore be seen that Herbert effects a compression which changes in accordance with the number of turns that the screw is threaded when the proximal threads are engaging bone.

SUMMARY OF THE INVENTION

It is an object of the invention to describe a bone screw having a distal portion and a proximal portion integrally interconnected by an intermediate portion. It is a further object of this invention to describe a bone screw having distal threads and proximal threads of the same pitch. It is an object of this invention to describe a bone screw having distal and proximal threads having self-cutting flutes. It is another object of this invention to describe a bone screw terminating in a sharp trocar point. It is an object of the invention to describe a bone screw having an intermediate portion with a substantially smooth outer surface. It is another object of this invention to describe a bone screw, particularly a fibular screw, having a cylindrical proximal shaft tapering into a tapered distal shaft.

It is a further object to provide a means for repair of a fracture running transverse to, or diagonally transverse to, the length of a long bone in which the repair medium compresses the fractured segments of the bone parallel to the length of the bone while maintaining a lengthwise alignment of the bone. It is a further object to provide a means for repairing such a bone in such a manner in which a screw is inserted so that a portion of the screw runs along the medullary canal of the bone, with the path of the screw ensuring that the bone segments remain in axial alignment, and in which the screw effects a longitudinal compression of the bone segments. It is yet a further object to describe a fibular screw which accomplishes this kind of compression, and which can be additionally used for repairs of lung bones other than the fibula.

The bone screw according to the invention is comprised of a proximal portion having a cylindrical proximal shaft and proximal threads. The proximal threads may be provided with self-cutting flutes in the form of notches. The proximal portion is provided with a means for engaging a tool such as a hexagonal opening for engaging a hexagonal screw driver designed to fit allen screws. The proximal portion integrally terminates into an intermediate portion having a substantially smooth outer surface tapering and integrally terminating into a distal portion. The distal portion has a distal tapering shaft terminating in a trocar point. The distal portion is provided with distal threads having the same pitch as the proximal threads. The distal threads also may be further provided with self-cutting flutes in the form of notches.

The screw is used by drilling a fractured long bone, such as a fibula, from the end thereof. The bore is enlarged at the entry point to a diameter sufficient for the proximal end of the screw to enter the bone, with the proximal end engaging the bone. It is significant that a portion of the purchase site which is to be engaged by the tapering intermediate portion is drilled narrower than the tapering portion, at least before the fracture line of the bone is reached.

By the distal threads engaging the bone beyond the fracture line when the tapering part of the intermediate portion is engaging the bone before the fracture line, a compressive force between the segments of the bone on opposite sides of the fracture line is established. This compressive force is maintained at least until the proximal threads engage the bone, thus establishing a compressed relationship between the bone segments engaged by the proximal and distal ends of the screw. Thus, compression is achieved by the profile of the screw rather than a differential thread pitch. An axial alignment of the bone segments is established as a result of the screw engaging the bone along the drill bore.

BRIEF DESCRIPTION OF THE DRAWING

These features and object of the invention will become apparent to those skilled in the art by referring to the accompanying drawing in which:

FIG. 1 is a perspective view of the fibular screw according to the invention;

FIG. 2 is a longitudinal sectional view of the fibular screw according to the invention;

FIG. 3 is a sectional view taken along lines 3—3 of FIG. 1;

FIG. 4 is a distal end view of the fibular screw according to the invention; and, FIGS. 5A-5E show a preferred technique for using the fibular screw according to the invention.

DETAILED DESCRIPTION OF THE PREFERRED EMBODIMENT

In order to more fully understand the invention, it should be pointed out that the words, "distal," and, "proximal," will be used to describe portions both of the screw and of the bone in the following manner:

When a fracture occurs at a portion of a long bone near an end of that bone furthest from the body, that fracture is said to occur at the distal, rather than the proximal end of the bone. On the other hand, the fibular screw will be described as being inserted in that end; the screw will be arranged so that the proximal end of the screw is adjacent the distal end of the bone. Therefore, the distal end of the screw will be the part of the screw that is closest to the proximal end of the bone. For this reason, the proximal and distal portions of the screw should not be confused with the proximal and distal ends of the bone, which are often, but not always, in opposite alignments.

The preferred form of the invention is shown as a distal fibular screw (i.e., a screw to be inserted into the distal end of the fibula) and includes a proximal portion 11, a distal portion 2 and an intermediate portion 3 integrally interconnecting the proximal portion 11 and distal portion 2. Preferably, the proximal portion 11 has a proximal shaft 11a which is cylindrical in shape. The proximal shaft 11a is provided with a plurality of proximal threads 4 having a given pitch.

The distal portion is comprised of a tapered distal shaft 2a terminating in a sharp trocar point 7. The distal portion 2 is provided with a plurality of distal threads 5. In the preferred embodiment, the distal threads may be provided with at least one self-cutting flute 6. The flute is preferably a notch which cuts through the threads 5, the notch having a wall 6a perpendicular to the distal shaft 2a and a wall 6b parallel to a tangent of the distal shaft 2a. The embodiment illustrated in FIGS. 1-4 utilize two such flutes 6 in the distal thread portion 2.

The proximal portion 11 is provided with a means for engaging a tool such as hexagonal opening 8 for engaging a hexagonal wrench. The intermediate portion 3 is integral with the proximal portion 11 and distal portion 2. The proximal portion 11 has a diameter which is greater than the greatest diameter of the distal portion. The proximal threads 4 may also include at least one self-cutting flute in the form of a notch 13 (FIGS. 1 and 4) such as those described for the distal threads. A particularly advantageous embodiment may include three notches 13 in the proximal portion and two flutes 6 in the distal portion.

In the embodiment shown, the proximal threads 4 have the same pitch as the distal threads 5. Regardless of the relative thread pitches, due to the tapered intermediate portion 3, a certain amount of compression can occur as the tapered area wedges into the bone or the medullary canal. That is, as the screw is applied to the bone the continuously increasing diameter of the intermediate portion causes compression between bone engaged by the intermediate portion 3 and the bone engaged by the distal threads 5. Preferably, the screw is threaded with relatively large threads, as illustrated to achieve substantial thread to bone contact. The screw is preferably made of a metal such as stainless steel.

Inasmuch as the tapered intermediate portion 3 is intended to effect compression, in the preferred embodiment, the intermediate portion 3 must be of sufficient length for at least a part of the intermediate portion 3 to engage the bone on one side of a fracture line while the distal threads 5 engage the bone at the other side of the fracture line. This would occur prior to the proximal threads 4 engaging the bone.

The tapered shaft 2a of the distal portion 2 is tapered slightly to conform to the narrow canal just above the lateral malleolus. The hexagonal opening 8 allows the proximal end of the screw to be engaged by a tool so that the screw can be recessed flush with the bone.

OPERATION AND SURGICAL PROCEDURE

Referring to FIGS. 5A-5E, a typical fracture 23 of the fibula 21 is shown. FIGS. 5A-5E illustrate a lateral view of the fibula. As is shown, fracture 23 will most likely occur along a fracture line near the distal end 25 of the bone, segmenting the fibula 21 into distal and proximal fragments 21d and 21p, respectively. In order to insert the screw, the distal end 25 is exposed by temporarily separating, to the extent necessary, the distal end 25 from the astragalus (not shown) and associated tendons and ligaments located at the distal end 25. After exposure of the distal end 25, the fibular is maintained in alignment and a center bore 27 is drilled along the length of the fibular 21 from the distal end. The bore 27 is sized so that the distal end of the bone screw will threadingly engage the bore. Preferably, the center bore 27 is drilled with a drill bit corresponding to the diameter of the leading tip end of the distal shaft 2a. The bore 27 is widened for a short distance from the distal end 25 in order to form a wider diameter portion 29 of the bore 27. The wider diameter portion 29 is preferably drilled with a bit corresponding to the diameter of the proximal shaft 11a. This wider portion 29 permits engagement of the threads 4 at the proximal portion of the screw, while allowing the screw to penetrate the outer cortex of the bone as the screw enters the distal end 25 of the bone.

After the purchase site is cleared of thrombosi and other debris, the screw 31 is inserted into the center bore 27 by using an allen key 33 or similar tool. While the allen key 33 is shown for simplicity, it is anticipated that an allen screwdriver will actually be used as the turning tool. When the distal threads 5 of the screw 31 have substantially cleared the fracture line 23, the taper at the intermediate portion 8 creates opposing forces, as indicated by arrows 35. As the tool 33 is rotated, these forces can continue to develop until the proximal threads 4 hold the bone 21 in the state of compression so established.

Compression of the distal bone fragment 21d onto the proximal bone fragment 21p is achieved as the distal threads 5 engage the proximal bone fragment 21p, as insertion continues and as the diameter of the intermediate portion 3 tapers to the larger diameter of the proximal portion 1, forcing the distal fragment of bone 21d (compressing the fracture) onto the proximal fragment 21p, pushing the distal portion 21d ahead. The compression takes place before the proximal threads 4 enter the bone 21.

Since, in the preferred embodiment, both sets of threads 4, 5 are of same pitch, as both sets of threads become engaged in the bone 21, no further compression is achieved because threads of the same pitch would be advancing the same amount. This is important because the engagement of the proximal threads 4 with the distal bone fragment 21d fixes the amount of bone compression established.

It should be clear that, although the compressive force may later subside as the bone tissue releases pressure against the distal threads 5 and the intermediate portion 3, the engagement of the proximal and distal threads 4, 5 with the bone 21 still provides a fixed relationship for the bone on either side of the fracture line 23. It should be further noted that, since the bore 27 and consequently the distal portion 2 of the screw 31 coincide with the medullary canal, a minimum of structural bone is lost in the narrow portion. This minimization of structural loss provides an increased strength of the bone 21 adjacent the distal portion 2 of the screw 31, that being the portion of the bone 21 where the reinforcement terminates and inherent bone strength is most needed.

While the placement of the proximal end 11 of the screw is mostly or entirely within cancellous bone, the distal end 2 is primarily placed in the cortical bone surrounding the medullary canal. Since the distal end 2 exerts a significant force on both the intermediate portion 3 and on the proximal end 11 of the screw, the included angle $\alpha$ of the thread cross-sections is critical. If that included angle $\alpha$ is less than 20°, than the threads have a reduced strength which would result in the threads collapsing, this being primarily a problem with the distal threads 5. If the included cross-sectional angles $\alpha$ is too great, the threads have a reduced purchasing power and would therefore have a tendency to "strip out" of both the cortical bone engaged by the distal threads and the cancellous bone engaged by the proximal threads. For this reason, the included angle $\alpha$ must be less than 60°. In the preferred embodiment, the included cross-sectional angle $\alpha$ is 40° which is within a preferred range of between 30° and 50°. Thus, the threads 5 at the distal end 2 are able to "grab" the cortical bone at the medullary wall, threads 4 at the proximal end 11 are able to maintain a satisfactory grip on the cancellous bone occuring at the distal end of the fibula. Thus, the proximal and distal threads 4, 5 are "cut" within the same included cross-sectional angle $\alpha$ and with the same pitch as described above.

It is contemplated that the screw may be supplied in different sizes. Generally, 90% of all fibular fractures occur just above the lateral malleolus (distal fibula) where the fibula "necks down". Often these fractures are comminuted. In the past, rush rods have been used, but these rods tend to rotate and back out. The disclosed fibular screw avoids this drawback by providing proximal and distal threads of the same pitch.

Various changes may be made in the details of the invention, as disclosed, without sacrificing the advantages thereof or departing from the scope of the appended claims. Furthermore, although the present invention has been disclosed and discussed with regard to its exceptional advantages in terms of a fibular screw, it may be understood that the invention may be employed in several surgical applications wherein a device for engaging two portions of bone is required. Thus, while the screw is particularly adapted for insertion along medullary canals of the long bones, but may also be used in a similar manner in bone other than just along the medullary canal.

I claim:

1. A compression bone screw comprising:
 (a) a distal portion including a distal shaft having a plurality of distal threads therein, the distal threads having a given pitch, said distal portion terminating in a substantially pointed end;
 (b) a proximal portion including a proximal shaft having a diameter which is greater than the diameter of the distal shaft said proximal portion including a tool interengaging means thereon; and
 (c) an intermediate portion connecting the proximal portion and the distal portion, the intermediate portion including a tapered shaft having a threadless substantially annular smooth outer surface, wherein the tapered shaft and the distal threads cooperate so as to create opposing forces which effect compression of bone tissue between the intermediate portion and the distal portion when the distal threads and the tapered shaft are both engaging bone tissue.

2. The bone screw of claim 1 wherein the proximal shaft is cylindrical, the distal shaft is tapered and the cross-sectional diameter of the proximal shaft is greater than the largest cross-sectional diameter of the distal shaft.

3. The bone screw of claim 2 wherein the cross-sectional diameter of the proximal shaft is no smaller than the largest cross-sectional diameter of the distal threads.

4. The bone screw of claim 2 wherein the distal threads are provided with at least one self-cutting flute.

5. The bone screw of claim 4 wherein the distal portion terminates in a sharp trocar point.

6. The bone screw of claim 2 wherein the distal threads may be inserted into a bore formed longitudinally along the center axis of the fractured end of a bone and, by inserting the screw into the bore until the distal threads engage the bone on one side of the fracture and at least a part of the intermediate portion is engaging the bone on the opposite side of the fracture, a compressive force is established in the bone parallel to the length of the screw, said distal portion terminating in a sharp trocar point.

7. The bone screw of claim 1 wherein the proximal shaft has a plurality of proximal threads thereon, said proximal threads having a given pitch which is the same as the given pitch of the distal threads.

8. The bone screw of claim 7 wherein the proximal threads are provided with at least one self-cutting flute.

9. The bone screw of claim 1 wherein the proximal portion is provided with a recessed socket for engaging a tool.

10. The bone screw of claim 9 wherein said recessed socket is a recessed hexagonal opening.

11. A compression bone screw comprising:
 (a) a distal portion including a distal shaft having a plurality of distal threads thereon, the distal threads being provided with at least one self-cutting flute, the distal threads having a given pitch, and the distal portion terminating in a sharp trocar point;
 (b) a proximal portion including a cylindrical proximal shaft having a plurality of proximal threads thereon, the proximal threads having the same given pitch as the distal threads, the proximal shaft having a diameter which is greater than the largest cross-sectional diameter of the distal threads; and the proximal portion being provided with a recessed socket adapted to be engaged by a tool for rotating said screw; and (c) an intermediate portion connecting the proximal portion and the distal portion, the intermediate portion including a tapered shaft having a threadless substantially annular smooth outer surface, wherein the distal threads may be inserted into a bore formed longitudinally along the center axis of a fractured bone and, by inserting the screw into the bore until the distal threads engage the bone on one side of the fracture and at least a part of the intermediate portion is engaging the bone on the opposite side of the fracture, the tapered shaft and the distal threads cooperate so as to create opposing forces which effect compression of bone tissue between the intermediate portion and the distal portion, the compressive force thus established being parallel to the length of the bone and the length of the screw, with the screw further establishing axial alignment of the bone at the fracture site.

12. The bone screw of claim 11, wherein said intermediate portion is of approximately the same length as said distal portion and said proximal portion.

13. A compression bone screw comprising:
(a) a distal portion including a distal shaft having a plurality of distal threads thereon, the distal threads having a given pitch;
(b) a proximal portion including a proximal shaft having a plurality of proximal threads thereon, the proximal shaft having a diameter which is greater than the diameter of the distal shaft, said proximal threads terminating about midway along said proximal shaft and
(c) an intermediate portion connecting the proximal portion and the distal portion, the intermediate portion including a tapered shaft having a substantially smooth outer surface, wherein the tapered shaft and the distal threads cooperate so as to create opposing forces which effect compression of bone tissue between the intermediate portion and the distal portion when the distal threads and the tapered shaft are both engaging bone tissue, said intermediate portion being of a approximately the same length as said distal portion and said proximal portion.

* * * * *